United States Patent [19]

Szkrybalo

[11] 3,981,860
[45] Sept. 21, 1976

[54] 2,3:4,5-DI-O-SUBSTITUTED GLUCONATES
[75] Inventor: William Szkrybalo, Verona, N.J.
[73] Assignee: Hoffmann-La Roche Inc., Nutley, N.J.
[22] Filed: June 20, 1974
[21] Appl. No.: 481,265

Related U.S. Application Data
[63] Continuation-in-part of Ser. No. 344,657, March 26, 1973, abandoned.

[52] U.S. Cl.................................. 536/4; 71/75; 71/76; 71/88; 424/181; 536/119
[51] Int. Cl.²........................................... C07H 9/04
[58] Field of Search............ 260/210 R, 340.9, 344, 260/657, 209 R, 234 R

[56] References Cited
UNITED STATES PATENTS

| | | |
|---|---|---|
| 3,451,993 | 6/1969 | Goshima et al.............. 260/210 R |
| 3,542,761 | 11/1970 | Rossi............................. 260/210 R |
| 3,586,650 | 6/1971 | Gibbons et al.............. 260/210 R |
| 3,592,808 | 7/1971 | Theander...................... 260/210 R |
| 3,598,804 | 8/1971 | Hindley et al................ 260/210 R |

Primary Examiner—Johnnie R. Brown
Attorney, Agent, or Firm—Samuel L. Welt; Bernard S. Leon; William M. Farley

[57] ABSTRACT

Plant growth regulant compounds represented by the formula:

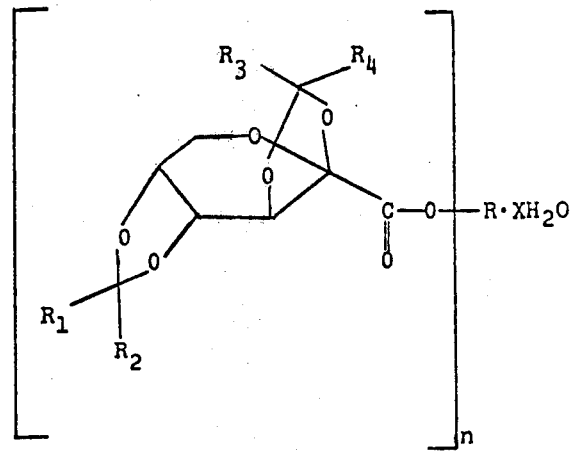

wherein, when $n$ is 1, R is hydrogen, sodium, potassium, ammonium, substituted ammonium, straight or branched chain aliphatic hydrocarbyl or halo-lower alkyl and, when n is 2, R is calcium, magnesium or lower alkylene, $R_1$, $R_2$, $R_3$ and $R_4$ are hydrogen, straight or branched chain aliphatic lower hydrocarbyl, halo-lower alky, aryl or $R_1$ and $R_2$ together and $R_3$ and $R_4$ together are each a saturated ring containing from 3 to 8 carbon atoms, $n$ is an integer from 1 to 2 and X is a number from 0 to 1; enantiomers and racemic mixtures.

These compounds are useful as post-emergence and pre-emergence plant growth regulants and herbicides.

45 Claims, No Drawings

2,3:4,5-DI-O-SUBSTITUTED GLUCONATES

RELATED APPLICATION

This application is a continuation-in-part of U.S. patent application Ser. No. 344,657, filed Mar. 26, 1973, now abandoned, the benefit of the date of which is hereby claimed.

BRIEF SUMMARY OF THE INVENTION

This invention relates to plant growth regulating and herbicidal compositions as well as methods for controlling plant growth, utilizing as the active ingredients 2,3:4,5-di-O-substituted-2-keto-D-gluconic acids as well as salts and esters thereof. Preferably, the active ingredients are 2,3:4,5-di-O-isopropylidene-2-keto-D-gluconic acid, its salts and esters. This invention also relates to novel 2,3:4,5-di-O-substituted-2-keto-D-gluconic acids as well as novel salts and esters thereof.

DETAILED DESCRIPTION OF THE INVENTION

The compounds which are active ingredients in the compositions and methods of this invention are represented by the formula:

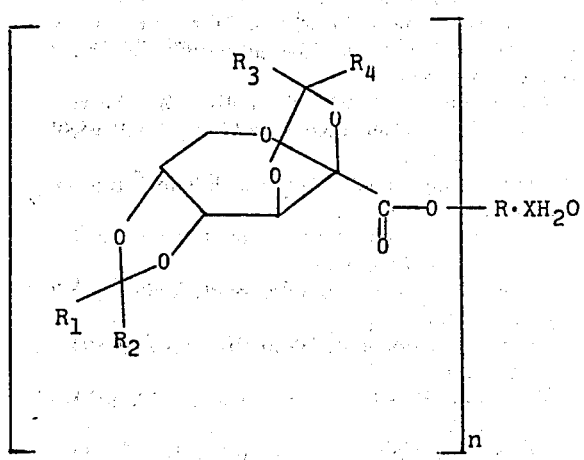

I wherein, when $n$ is 1, R is hydrogen, sodium potassium, ammonium, substituted ammonium, straight or branched chain aliphatic hydrocarbyl or halo-lower alkyl and, when $n$ is 2, R is calcium, magnesium or lower alkylene, $R_1$, $R_2$, $R_3$ and $R_4$ are hydrogen, straight or branched chain aliphatic lower hydrocarbyl, halo-lower alkyl, aryl or $R_1$ and $R_2$ together and $R_3$ and $R_4$ together are each a saturated ring containing from 3 to 8 carbon atoms, $n$ is an integer from 1 to 2 and X is a number from 0 to 1, enantiomers and racemic mixtures.

The plant growth regulant compounds which are preferred for use in this invention because of their post-emergent plant growth regulant activity are represented by the formula:

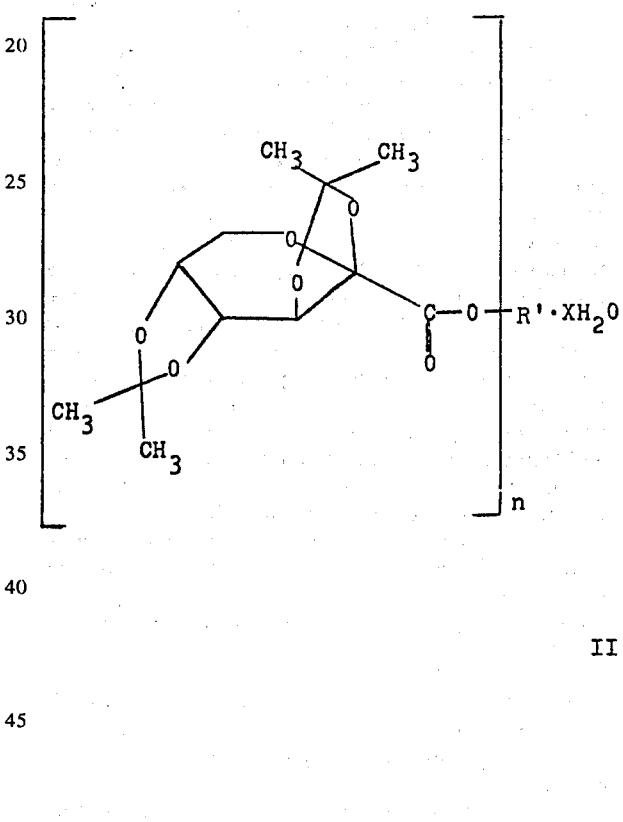

II wherein, when $n$ is 1, R' is hydrogen, sodium, potassium, ammonium, substituted ammonium, straight or branched chain aliphatic hydrocarbyl or halo-lower alkyl and, when $n$ is 2, R' is calcium, magnesium or lower alkylene, $n$ is an integer from 1 to 2 and X is a number from 0 to 1, enantiomers and racemic mixtures.

The compounds represented by formulas I and II are all of the D configuration since they are derived from the naturally occurring 2-ketohexose, D-fructose. While D-fructose is the only known naturally occurring form of fructose, its enantiomer, L-fructose, can be synthesized. It should be noted that compounds with the L-configuration and racemic mixtures of the compounds can be made using either L-fructose or a mixture of D- and L-fructose in identical preparatory procedures as for the D-configuration as discussed hereinafter.

All structural formulas set forth herein are for convenience only and are not intended to depict any absolute configuration. The formulas cover enantiomers and racemic mixtures. The Examples and other description, unless specifically noted otherwise, are directed to the racemic compounds.

The compounds represented by Formulae I and II have post-emergent and/or pre-emergent plant growth regulant activity and herbicidal activity. However, the post-emergent plant growth regulant activity is much more significant since most of the compounds have this activity and since it provides a means for control of the growth of weeds which appear in turf.

As used herein, "plant growth regulant" means a compound or composition which affects the maturation and metabolism of plants. Hence, a "plant growth regulant" has many effects on plant growth. However, not all plant growth regulant active compounds affect plants the same way. For example, they could affect vegetative growth by retarding or stimulating terminal growth, and/or stimulating side branching and could inhibit new growth such as the development of new sprouts of woody plants, the sprouting of tubers and rhizomes and the development of sucker growth. Such regulants could affect flowering plants by eliminating early flowering, by thinning of blossoms or by increasing the number of flowers. Fruit-bearing trees and bushes could be affected by increases in the number, size and quality of the fruit, by producing seedless fruit, by accelerating senescence and fruit ripening and by stimulating fruit and/or leaf abscission. Both flowering and fruit plants could be affected by accelerating plant dormancy and maintaining bud dormancy. A "plant growth regulant" could cause selective post-emergent control of weeds by reducing their vigor and competitiveness and, thus, prevent their spread and stop normal seeding.

Some specific applications of plant growth regulants include preventing lodging of cereals;

increasing production of harvestable tea leaves by promoting side branching;

inhibiting sprouting of potatoes and onions in storage;

suppressing growth of grass, trees, shrubs, and other vegetation in decorative lawn areas, parks, golf courses and along highways and other rights-of-way;

accelerating fruit ripening and thus, aiding mechanical harvesting a single or reduced number of pickings;

defoliating cotton to permit mechanical harvest;

inhibiting new growth of defoliated cotton and, thus, reducing staining of fiber during mechanical harvesting;

increasing the quality of the harvested crop, e.g., sugar content of sugar cane, sugarbeets, grapefruit, grapes, and other fruits;

aiding mechanical harvesting of nut crops by accelerating ripening, stimulating husk cracking and promoting abscission;

protecting crops from drought;

protecting fruit crops from frost by stimulating early dormancy and/or preventing premature breaking of dormancy;

increasing latex flow of rubber;

increasing frost resistance of winter cereals;

reducing the flowering or bolting of lettuce, sugar beets and tobacco;

controlling tobacco suckering;

stimulating increased fruit set of soybeans, peanuts, cotton, tomatoes, melons, and other fruits and enhancing fruit color and quality.

stimulating branching of pot plants, e.g. heather, azalea, chrysanthemum and geranium;

growth retardation in pot plants, e.g. poinsettia, petumia and chrysanthemum;

stimulating branching of young fruit trees, e.g. apple and pear.

As used herein, the term "straight or branched chain aliphatic hydrocarbyl" denotes a monovalent substituent having from 1 to 20 carbon atoms consisting solely of carbon and hydrogen and which contains no aromatic unsaturation but which can be otherwise saturated or unsaturated, i.e., alkyl, alkenyl or alkynyl group. The term "lower alkylene" denotes a divalent substituent consisting of straight and branched chain aliphatic hydrocarbons of from 1 to 7 carbon atoms and having its valence bonds from different carbons. As applied to these groups, the term "lower" denotes a group having a carbon skeleton containing from 1 to 7 carbon atoms. The term "lower alkyl" includes both straight and branched chain saturated aliphatic groups containing from 1 to 7 carbon atoms, such as methyl, ethyl, n-propyl, isopropyl, n-butyl and the like. "Substituted ammonium" refers to ammonium radicals in which one or more of the hydrogens has been replaced by a lower alkyl, lower alkenyl or hydroxyalkyl substituent. The term "aryl" refers to an aromatic hydrocarbon such as phenyl and phenyl radicals having one or more alkyl, alkenyl, alkinyl, alkoxy or halo-lower alkoxy substituents thereon. "Halo-lower-alkyl" means a lower alkyl group in which one or more of the hydrogens is replaced by a halogen, preferably fluorine, chlorine or bromine.

Representative of the compounds within the scope of Formula I which are active as plant growth regulants and herbicides are:

2,3-O-isopropylidene-4,5-O-benzylidene-2-keto-D-gluconic acid;

2,3-O-isopropylidene-4,5-O-(p-methoxybenzylidene)-2-keto-D-gluconic acid;

2,3-O-isopropylidene-4,5-O-(3-pentylidene)-2-keto-D-gluconic acid;

2,3-O-isopropylidene-4,5-O-methylene-2-keto-D-gluconic acid;

2,3-O-isopropylidene-4,5-O-ethylidene-2-keto-D-gluconic acid;

2,3-O-isopropylidene-4,5-O-(2-butylidene)-2-keto-D-gluconic acid;

2,3-O-isopropylidene-4,5-O-cyclohexylidene-2-keto-D-gluconic acid;

2,3:4,5-di-O-(3-pentylidene)-2-keto-D-gluconic acid;

2,3:4,5-di-O-ethylidene-2-keto-D-gluconic acid;

2,3:4,5-di-O-benzylidene-2-keto-D-gluconic acid;

2,3:4,5-di-O-(p-methoxy-benzylidene)-2-keto-D-gluconic acid;

2,3-O-isopropylidene-4,5-O-(2-chloroethylidene)-2-keto-D-gluconic acid;

2,3-O-isopropylidene-4,5-O-(1,3-dichloroisopropylidene)-2-keto-D-gluconic acid;

2,3-O-isopropylidene-4,5-O-(1,1,3-trichloroisopropylidene)-2-keto-D-gluconic acid;

2,3-O-isopropylidene-4,5-O-(1,1,1,3-tetrachloroisopropylidene-2-keto-D-gluconic acid;

2,3-O-isopropylidene-4,5-O-(2,2-dichloroethylidene)-2-keto-D-gluconic acid;
2,3-O-isopropylidene-4,5-O-(1,1,3,3-tetrachloroisopropylidene)-2-keto-D-gluconic acid;
2,3-O-isopropylidene-4,5-O-(1,1,1,3,3-pentachloroisopropylidene)-2-keto-D-gluconic acid;
2,3-O-isopropylidene-4,5-O-(2,2,2-trichloroethylidene)-2-keto-D-gluconic acid;
2,3-O-isopropylidene-4,5-O-(1,1,1,3,3,3-hexachloroisopropylidene)-2-keto-D-gluconic acid;
2,3-O-isopropylidene-4,5-O-(2-fluoroethylidene)-2-keto-D-gluconic acid;
2,3-O-isopropylidene-4,5-O-(1,3-difluoroisopropylidene)-2-keto-D-gluconic acid;
2,3-O-isopropylidene-4,5-O-(1,1,3-trifluoroisopropylidene)-2-keto-D-gluconic acid;
2,3-O-isopropylidene-4,5-O-(1,1,1,3-tetrafluoroisopropylidene)-2-keto-D-gluconic acid;
2,3-O-isopropylidene-4,5-O-(2,2-difluoroethylidene)-2-keto-D-gluconic acid;
2,3-O-isopropylidene-4,5-O-(1,1,3,3-tetrafluorisopropylidene)-2-keto-D-gluconic acid;
2,3-O-isopropylidene-4,5-O-(1,1,1,3,3-pentafluoroisopropylidene)-2-keto-D-gluconic acid;
2,3-O-isopropylidene-4,5-O-(2,2,2-trifluoroethylidene)-2-keto-D-gluconic acid;
2,3-O-isopropylidene-4,5-O-(1,1,1,3,3,3-hexafluoroisopropylidene)-2-keto-D-gluconic acid;
2,3-O-isopropylidene-4,5-O-(2-bromoethylidene)-2-keto-D-gluconic acid;
2,3-O-isopropylidene-4,5-O-(1,3-dibromoisopropylidene)-2-keto-D-gluconic acid;
2,3-O-isopropylidene-4,5-O-(1,1,3-tribromoisopropylidene)-2-keto-D-gluconic acid;
2,3-O-isopropylidene-4,5-O-(2,2-dibromoethylidene)-2-keto-D-gluconic acid;
2,3-O-isopropylidene-4,5-O-(1,1,3,3-tetrabromoisopropylidene)-2-keto-D-gluconic acid;
2,3-O-isopropylidene-4,5-O-(2,2,2-tribromoethylidene)-2-keto-D-gluconic acid;
2,3-O-isopropylidene-4,5-O-(1,1,1-tribromoisopropylidene)-2-keto-D-gluconic acid;
2,3:4,5-di-O-(2-chlorooethylidene)-2-keto-D-gluconic acid;
2,3:4,5-di-O-(1,3-dichloroisopropylidene)-2-keto-D-gluconic acid;
2,3:4,5-di-O-(1,1,3-trichloroisopropylidene)-2-keto-D-gluconic acid;
2,3:4,5-di-O-(1,1,1,3-tetrachloroisopropylidene)-2-keto-D-gluconic acid;
2,3:4,5-di-O-(2,2-dichloroethylidene)-2-keto-D-gluconic acid;
2,3:4,5-di-O-(1,1,3,3,-tetrachloroisopropylidene)-2-keto-D-gluconic acid;
2,3:4,5-di-O-(2,2,2-trichloroethylidene)-2-keto-D-gluconic acid;
2,3:4,5-di-O-(2-fluoroethylidene)-2-keto-D-gluconic acid;
2,3:4,5-di-O-(1,3-difluoroisopropylidene)-2-keto-D-gluconic acid;
2,3:4,5-di-O-(1,1,3-trifluoroisopropylidene)-2-keto-D-gluconic acid;
2,3:4,5-di-O-(1,1,1,3-tetrafluoroisopropylidene)-2-keto-D-gluconic acid;
2,3:4,5-di-O-(2,2-difluoroethylidene)-2-keto-D-gluconic acid;
2,3:4,5-di-O-(1,1,3,3-tetrafluoroisopropylidene)-2-keto-D-gluconic acid;
2,3:4,5-di-O-(1,1,1,3,3-pentafluoroisopropylidene)-2-keto-D-gluconic acid;
2,3:4,5-di-O-(2,2,2-trifluoroethylidene)-2-keto-D-gluconic acid;
2,3:4,5-di-O-(1,1,1,3,3,3-hexafluoroisopropylidene)-2-keto-D-gluconic acid;
2,3:4,5-di-O-(2-bromoethylidene)-2-keto-D-gluconic acid;
2,3:4,5- di-O-(1,3-dibromoisopropylidene)-2-keto-D-gluconic acid;
2,3:4,5-di-O-(1,1,3-tribromoisopropylidene)-2-keto-D-gluconic acid;
2,3:4,5-di-O-(2,2-dibromoethylidene)-2-keto-D-gluconic acid;
2,3:4,5-di-O-(1,1,3,3-tetrabromoisopropylidene)-2-keto-D-gluconic acid;
2,3:4,5-di-O-(2,2,2-tribromoethylidene)-2-keto-D-gluconic acid;
2,3:4,5-di-O-(1,1,1-tribromoisopropylidene)-2-keto-D-gluconic acid;
2-keto-D-gluconic acid monohydrate;
2,3:4,5-di-O-cyclohexylidene-2-keto-D-gluconic acid;
2,3:4,5-di-O-(2-butylidene)-2-keto-D-gluconic acid;
2,3:4,5-di-O-methylene-2-keto-D-gluconic acid;

In addition, salts, e.g. alkaline, alkaline earth, ammonium and substituted ammonium, and esters, e.g. lower alkyl, lower alkenyl and lower alkinyl, of the above compounds are also active as plant growth regulants and herbicides.

Representative of the preferred compounds within the scope of Formula II are:
methyl-2,3:4,5-di-O-isopropylidene-2-keto-D-gluconate;
ethyl-2,3:4,5-di-O-isopropylidene-2-keto-D-gluconate;
n-butyl-2,3:4,5-di-O-isopropylidene-2-keto-D-gluconate;
n-propyl-2,3:4,5-di-O-isopropylidene-2-keto-D-gluconate;
isopropyl-2,3:4,5-di-O-isopropylidene-2-keto-D-gluconate;
n-dodecyl-2,3:4,5-di-O-isopropylidene-2-keto-D-gluconate;
n-pentyl-2,3:4,5-di-O-isopropylidene-2-keto-D-gluconate;
calcium-2,3:4,5-di-O-isopropylidene-2-keto-D-gluconate;
n-decyl-2,3:4,5-di-O-isopropylidene-2-keto-D-gluconate;
benzyl-2,3:4,5-di-O-isopropylidene-2-keto-D-gluconate;
isoamyl-2,3:4,5-di-O-isopropylidene-2-keto-D-gluconate;
2-butyl-2,3:4,5-di-O-isopropylidene-2-keto-D-gluconate;
2-bromoethyl-2,3:4,5-di-O-isopropylidene-2-keto-D-gluconate;
N-ethanolammonium-2,3:4,5-di-O-isopropylidene-2-keto-D-gluconate;
Bis-2,3:4,5-di-O-isopropylidene-2-keto-D-gluconate, ethylene glycol ester.
2,3:4,5-di-O-isopropylidene-2-keto-D-gluconic acid monohydrate;
allyl-2,3:4,5-di-O-isopropylidene-2-keto-D-gluconate;
sodium-2,3:4,5-di-O-isopropylidene-2-keto-D-gluconate;
potassium-2,3:4,5-di-O-isopropylidene-2-keto-D-gluconate;

ammonium-2,3-4,5-di-O-isopropylidene-2-keto-D-gluconate;
dimethylammonium-2,3:4,5-di-O-isopropylidene-2-keto-D-gluconate.

The active compounds are useful in plant growth regulating compositions for controlling growth of grasses and weeds as well as other undesired plants which become inadvertently mixed in with the desired crops. While the compounds have pre-emergent growth regulant activity, they are most useful when used for post-emergent control. The post-emergent efficacy of the active compounds of this invention is apparent from their control of undesired plants. For example, in the post-emergent control of crabgrass, a weed which heretofore has not been effectively controlled by post-emergent herbicides the active compounds of this invention slow down the growth and maturation of crabgrass and by thus preventing its seeding, effectively prevent its spread.

In the control of grasses, particularly home lawns and industrial turfs, e.g. golf courses, it has been established that a maximum growth retardation as evidenced by diminished grass height as compared to an untreated control of about 40%–60% is desirable with about 50% growth retardation preferred. Any retardation less than 40% is ineffective in that grass control is not substantial enough to have a significant aesthetic effect and to reduce or eliminate manual care. On the other hand, retardation greater than 60% results in an undesired skimpy appearance to the lawn or turf with subsequent invasion thereof by weeds and other undesirable plants.

The active compounds show herbicidal activity especially against composite weeds, e.g., matricaria species and other weeds such as *papaver rhoeas*, *stellaria media* and *caprella bursa pastoris*.

The active compounds useful in this invention are particularly active against the following plants:

a. grasses such as *Agropyron repens*, *Bromus inermis*, *Bromus erectus*, *Deschampsia flexuosa*, *Alopecurus pratensis*, *Arrhenatherum elatius*, *Dactylis glomerata*, *Festuca pratensis*, *Trisetum flavescens*, *Holcus lanatus*, *Lolium perenne*, *Poa annua*, *Poa neumoralis*, *Festuca ovina*, *Festuca rubra*, *Festuca nigrescens*, *Cynosurus cristatus*, *Agrostis schraderiana*, *Agrostis stolonifera*, *Phleum pratense*, *Phleum nodosum*, *Cynodon dactylon*, sugar cane and cereals such as corn, rice, wheat, rye, barley, oats and sorghum;

b. trees and shrubs such as fruit trees e.g., apple, pear, peach, cherry and citrus, as well as cocoa, tea, coffee, banana and rubber trees;

c. ornamental plants such as privet, horn-beam, white cedar, juniper, rose, azalea, chrystanthemum, poinsethia, cyclamen, pyracantha, forsythia and magnolia;

d. field crops such as cotton, soya beans, peanuts, tobacco and flax;

e. vegetables such as solanacease, e.g., tomatoes, legumes and cucumbers;

f. berries such as strawberries, blackberries, blueberries, cranberries, raspberries and currants.

In addition they are also useful for reducing pruning requirements in viticulture.

In order to effect uniform distribution of the active compound of the growth regulating compositions according to this invention, the compound can be mixed with conventional herbicidal adjuvants, modifiers, diluents, or conditioning agents so that they may be formulated as solutions, emulsions, dispersions, dusts or wettable powders.

Liquid formulations of the active compounds for direct spraying may be made, for example, as aqueous solutions containing a wetting agent such as 1% Tween or as solutions in solvent mixtures containing acetone, methanol and dimethyl formamide (DMF) in the ratio of 90:8:2, volume/volume.

Emulsions can be prepared containing 25–50% of the active ingredient, and surface active agents, e.g., wetting agents, dispersing agents, emulsifying agents and the like, in sufficient amounts to impart the desired characteristics to the formulation.

The compounds can also be formulated as spray solutions from wettable powders using an inert diluent, e.g., kaolin. A typical spray solution formulated with a wettable powder, would, thus contain the active ingredient, from about 1% to about 5% of an inert diluent, minor amounts of dispersing, wetting and anti-foaming agents and, the balance, water.

Different forms of application may be better adapted to the various purposes for which the active compounds are to be used by the addition of substances which improve dispersion, adhesion, resistance to rain and penetrative power such as fatty acids, resins, wetting agents, emulsifying agents, glue and the like. In a similar manner, the biological spectrum may be broadened by the addition of substances having bactericidal, herbicidal, and fungicidal properties and also by combination with fertilizers, chelating agents and other plant growth regulators.

Representative of herbicides and plant growth regulants which may be admixed with the compounds of this invention are:

2,2-dichloropropionic acid
N-(4-aminobenzenesulphonyl) methylcarbamate
2-chloro-4-ethylamino-6-isopropylamino-1,3,5-triazine
4-chloro-2-oxobenzothiazolin-3-ylacetic acid
5-bromo-6-methyl-3-(1-methyl-n-propyl) uracil
3,5-dibromo-4-hydroxybenzonitrile
D-N-ethyl-2-(phenylcarbamoyloxy) propionamide
N-(4-bromo-3-chlorophenyl)-N'-methoxy-N'-methylurea
2-chloro-9-hydroxyfluorene-9-carboxylic acid
N'-4-(4-chlorophenoxy) phenyl-NN-dimethylurea
isopropyl N-(3-chlorophenyl) carbamate
2,3,5,6-tetrachloroterephthalic acid dimethyl ester (DCPA)
2,4-dichlorophenoxyacetic acid
4-isopropylamino-6-methylamino-2-methylthio-1,3,5-triazine
3,6-dichloro-2-methoxybenzoic acid
(±) 2-(2,4-dichlorophenoxy) propionic acid
9,10-dihydro-8a, 10a-diazoniaphenanthrene-2A
N'-(3,4-dichlorophenyl)-NN-dimethylurea
gibberellic acid
indolylacetic acid
indolybutyric acid
4-hydroxy-3,5-di-iodobenzonitrile
N'-(3,4-dichlorophenyl)-N-methoxy-N-methylurea
4-chloro-2-methylphenoxyacetic acid
4-(4-chloro-2-methylphenoxy) butyric acid
(±) 2-(4-chloro-2-methylphenoxy) propionic acid
N-(benzothiazol-2-yl)-NN'-dimethylurea
N'-(3-chloro-4-methoxyphenyl)-NN-dimethylurea
1,2,3,6-tetrahydro-3,6-dioxopyridazine
N'-(4-chlorophenyl)-N-methoxy-N-methylurea
N'-(4-chlorophenyl)-NN-dimethylurea napthylacetic acid
N-1-naphthylphtalamic acid
2,4-dichlorophenyl 4-nitrophenyl ether
1,1'-dimethyl-4,4'-bipyridylium-2A
3-(m-tolylcarbamoyloxy)phenyl carbamate
4-amino-3,5,6-trichloropicolinic acid
4,6-bisisopropylamino-2-methylthio-1,3,5-triazine
N-(3,4-dichlorophenyl) propionamide
isopropyl N-phenylcarbamate
5-amino-4-chloro-2-phenylpyridazin-3(2H)-one
2-chloro-4,6-bisethylamino-1,3,5-triazine
sodium nonochloroacetate
2,4,5-trichlorophenoxyacetic acid
5-chloro-6-methyl-3-t-butyluracil
4-ethylamino-2-methylthio-6-t-butylamino-1,3,5-triazine (terbutryn)
2,3,5-triiodobenzoic acid
1,1,4-trimethyl-6-isopropyl-5-propionyl-indane Representative fungicides which may be admixed with the compounds of this invention are:
2,4-Dichloro-6-(o-chloroaniline)-S-triazine
2,4,5,6-Tetrachloroisophthalonitrile
p-Dimethylaminobenzenediazo sodium sulfonate
1,4-Dichloro-2,5-dimethoxybenzene
Manganous-ethylene-bisdithiocarbamate
Zinc-manganous-ethylene-bisdithiocarbamate
Coordination product of zinc and manganese-ethylene-bisdithiocarbamate
Methyl-1(butylcarbamoyl)-2-benzimidazol-carbamate
2-(4-thiazol)-benzimidazol
cis-N-[(trichloromethyl)-thio]-4-cyclohexene-1,2-dicarboximide Rates of application are based upon the results reported herein and are not to be deemed all-inclusive since many extraneous factors can alter the rates of application. For example, rates may vary not only among different plant species but also within a particular species depending on such factors as plant size and age, the compound used, the time of year, type of soil and such climatological conditions at application time as air temperature, rainfall and winds. In addition, if the compounds or compositions are applied via a soil drench, higher concentrations would be needed since this type of application is indirect in comparison to a direct application, upon leaves and stems, e.g. spraying.

The amounts of active inredients in the growth regulating compositions of this invention thus varies according to the plants to be controlled, the requisite application rate, type of application the active compound used and the control desired. Generally, the compositions contain less than 50% active compound.

Basically, the application rate of the active compound is that which is effective in providing the requisite growth regulant control to the plant. For example, as noted earlier an effective growth regulant amount for grasses is that amount which will retard grass height growth to be 40%–60% of the normal growth rate. Hence, the choice of the minimum applicatio rate would be determined by the minimum amount of active compound which is effective in regulating growth to the lowest limit of the desired growth retardation range. The choice of the maxiumum application rate would be determined as that amount which is effective in regulating growth to the upper limit of the desired growth retardation range, i.e., in the case of lawn and turf grasses, that amount above which a skimpy appearance to the turf or lawn results, or which prevents all subsequent growth.

With tomato plants, the criteria for effective growth retardant amount are different since a dwarfed, bushy plant wherein there is no loss of fruit quality or quantity is considered desirable. The parameters for effective growth regulant activity for such plants are retarded terminal growth and enhanced or non-retarded lateral growth as the minimum effects and retarded terminal and lateral growth as the maximum effects. Application rates of active compounds which have these desired effects on tomato plant growth are determined with these criteria in mind. In order to obtain the greatest post-emergent growth regulating activity, application rates of from 0.5 pound to 20 pounds or more per acre generally are needed based on the weight of the active compound. The greatest post-emergence growth regulating activity is normally obtained with application rates of from about 1 to 15 pounds or more of active ingredient per acre. A preferred dosage range in solutions for spray application is from 100 to 10,000 ppm depending on the species to be treated and the active compound utilized with the most preferred range generally being 100 to 1,000 ppm.

An additional advantage in the use of the active compounds of this invention is the absence of any permanent effect on plants or any regulant residue in the soil. As the compounds undergo slow decomposition, there is a consequent diminution of activity. Such an effect is advantageous in that a. a short-term effect, which can be lengthened by subsequent additional application, is attained;
b. normal growth activity resumes as the regulant activity decreases; and
c. no deleterious residues remain on the plants or in the soil.

The length of the retardant effect varies with the compound used and other factors such as the plant species, climatological conditions, etc.

Although exhibiting plant growth regulant and herbicidal activity, the active compounds are virtually non-toxic to animals. The decomposition products, initially 2-keto-D-gluconic acid and finally carbohydrates, are also non-toxic.

It will be appreciated, of course, that all of the compounds represented by Formulas I and II are not active against all plants. However, each of the active compounds within the scope of this invention has activity against a specific plant or plants which is a function of the compound. As will be seen hereinafter, one advantage of this invention is that it provides a series of compositions which when applied to various plants as noted earlier supplies pre-emergent and post-emergent growth regulating activity and herbicidal activity on a wide spectrum of plants. Growth regulant activity of the active compounds of the instant invention is exemplified in the following microscreen test for post-emergence effects.

A. Evaluation of 2,3:4,5-di-O-isopropylidene-2-keto-Dgluconic acid and its ammonium salt Growth retardant studies using 2,3:4,5-di-O-isopropylidene-2-keto-D-gluconic acid were made on a variety of plants.

Plants to be tested are grown in potting compost in plastic pots. Seeds are planted so that all species reach the required growth stage for testing at the same time. The plants are grown in greenhouses and remain there during the entire test period with daylight supplemented, if necessary, by mercury vapor lamps to provide a 16 hour day.

The active compound is formulated as a spray from a wettable powder with kaolin as the inert diluent in the following proportions:

1% 2,3:4,5-di-O-isopropylidene-2-keto-D-gluconic acid
2.5% kaolin
96% water
plus small amounts of wetting and antifoaming agents.

This spray solution is applied to the plants at a 10 kilogram of active ingredient per hectare rate. This is equivalent to about 11 pounds per acre. Growth retardation is measured by observations, made 21 days after sprying, as to plant height compared to an untreated control. Results for the various plants are tabulated in Table I below.

TABLE I

| Plant Species | Plant Height, mm, 21 days after spraying | |
|---|---|---|
| | Untreated Control | 2,3:4,5-di-O-isopropylidene-2-keto-D-gluconic acid |
| Avena fatua | 400 | 420 |
| Echinochloa crus-galli | 360 | 260 |
| Fagopyrum vulgare | 430 | 150 |
| Sorghum vulgave | 200 | 160 |
| Sinapis alba | 300 | 130 |
| Setaria faberii | 280 | 90 |
| Datura stramonium | 160 | 120 |
| Alopecurus pratensis | 380 | 80 |
| Chrysanthemum segetum | 130 | 60 |
| Rumex obtusifolius | 200 | 70 |
| Stellaria media | 150 | 100 |
| Daucus carota | 170 | 160 |

This data show the activity of 2,3:4,5-di-O-isopropylidene-2-keto-D-gluconic acid as a plant growth regulant for a variety of plants. For example, with *Alopecurus pratensis*, a grass closely related to a lawn grass, excellent retardation was achieved without any chlorosis (i.e.—yellowing of grass). With *Chrysanthemum segetum*, there was excellent growth control without any damage to the plant.

Tables II and III below list data on a plant spectrum of 12 crops and weeds evaluated for both pre-emergence and post-emergence growth retardant effects after spray application of a water solution of the ammonium salt of 2,3:4,5-di-O-isopropylidene-2-keto-D-gluconic acid.

The ammonium salt is diluted in deionized water containing 1% Tween 20 (polyoxysorbitan monostearate) as a surfactant with the final pH adjusted to 7.0. Atrazine (2-chloro-4-(ethylamino)-6-(isopropylamino)-5-triazine), applied, at the rate of 2 pounds per acre, as a solvent mixture in acetone, methanol and DMF (90:80:2 v/v), is used as the reference standard for both the pre-emergence and post-emergence studies.

The crop and weed species are seeded in individual 3 inch plastic pots.

For the pre-emergence evaluation, the seeds are covered with sand rather than soil to increase the sensitivity of the testing. Soil depth is about 1.75 inches and the sand depth is about 0.2–0.25 inches.

For post-emergence evaluation, a sandy loam soil type is used and seeding-time is adjusted so that the plants reach suitable growth development, usually the first true leaf stage, at approximately the same time.

Both pre-emergence and post-emergence evaluations are made at an 8 pound per acre rate. Observations are made after 21 and 27 days for the pre-emergence study and after 18 and 27 days for the post-emergence study.

The results of these evaluations are listed in Tables II and III wherein the retardant response rating is set forth numerically. The rating code is as follows:

| | | |
|---|---|---|
| 0 | - | no visible retardation |
| 1, 2, 3 | - | slight retardation, plants have little or no reduction in top growth |
| 4, 5, 6 | - | moderate retardation, plants have reduced top growth |
| 7, 8, 9 | - | severe retardation, plants have little to no growth |
| 10 | - | no growth. |

TABLE II

Pre-Emergence Growth Retardant Effect of the Ammonium Salt of 2,3:4,5-di-O-isopropylidene-2-keto-D-gluconic acid

| | Retardant Response Rating | | | |
|---|---|---|---|---|
| | After 21 days | | After 27 days | |
| Plant | $NH_4^+$ salt | Atrazine Standard | $NH_4^+$ salt | Atrazine Standard |
| Yellow Nutsedge | 8 | 4 | 8 | 5 |
| Wild Oats | 2 | 10 | 1 | 10 |
| Jimsonweed | 4 | 5 | 2 | 9 |
| Velvetleaf | 3 | 10 | 3 | 10 |
| Johnson grass | 5 | 0 | 4 | 0 |
| Pigweed | 2 | 8 | 2 | 9 |
| Mustard | 3 | 10 | 3 | 10 |
| Yellow Foxtail | 6 | 9 | 6 | 9 |
| Barnyard grass | 6 | 10 | 7 | 10 |
| Crabgrass | 6 | 10 | 8 | 10 |
| Canada Thistle | 4 | 9 | 4 | 10 |
| Morning glory | 3 | 8 | 2 | 10 |

As a pre-emergence growth retardant, the ammonium salt of 2,3:4,5-di-O-isopropylidene-2-keto-D-gluconic acid thus shows good activity against certain species, e.g., yellow nutsedge, barnyard grass and crabgrass.

TABLE III

Post-Emergence Growth Retardant Effect of the Ammonium Salt of 2,3:4,5-di-O-isopropylidene-2-keto-D-gluconic acid

| | Retardant Response Rating | | | |
|---|---|---|---|---|
| | After 18 days | | After 27 days | |
| Plant | $NH_4^+$ salt | Atrazine Standard | $NH_4^+$ salt | Atrazine Standard |
| Yellow nutsedge | 5 | 10 | 9 | 10 |
| Wild Oats | 4 | 10 | 4 | 10 |
| Jimsonweed | 4 | 10 | 8 | 10 |
| Pigweed | 7 | 10 | 5 | 10 |
| Johnson grass | 5 | 5 | 7 | 4 |
| Bindweed | 4 | 8 | 5 | 7 |
| Mustard | 8 | 10 | 10 | 10 |
| Yellow Foxtail | 6 | 9 | 5 | 10 |
| Barnyard grass | 6 | 10 | 8 | 10 |
| Crabgrass | 8 | 9 | 9 | 10 |
| Soybean | 5 | 10 | 7 | 10 |
| Morning glory | 9 | 10 | 9 | 10 |

As a post-emergence growth retardant, the ammonium salt of 2,3:4,5-di-O-isopropylidene-2-keto-D-gluconic acid shows excellent activity at the 8 pounds per acre level against most of the species tested. The ammonium salt was particularly effective against pigweed, bindweed and crabgrass.

2,3:4,5-di-O-isopropylidene-2-keto-D-gluconic acid is prepared from the oxidation of the intermediate 2,3:4,5-di-O-isopropylidene-β-D-fructopyranose which is in turn prepared by the reaction, in acidic media, of D-fructose with acetone. The procedure for preparing the intermediate diisopropylidene-fructopyranose is essentially that described in U.S. Pat. No. 3,607,862.

Salts of this acid are prepared by conventional processes wherein the acid is added with rapid stirring to an aqueous solution of a base at room temperature. The solution is monitored to maintain pH above 7. Upon completion of the reaction, excess water is removed under high vacuum. Anhydrous acetone is then added to the resulting syrup (about 10 volumes) with overnight stirring. The white crystalline precipitate which forms is filtered, washed with acetone and dried. In the case of the non-volatile bases, equivalent amounts of acid are admixed. For the volatile bases, e.g. $NH_4OH$ and $(CH_3)_2NH$, excess base is added and the excess is subsequently removed in the vacuum evaporation.

Since the acid is not stable under normal esterification conditions such as the Fischer esterification procedure, the novel esters are prepared by reaction with the appropriate lower alkyl, lower alkenyl or lower alkinyl halide under basic conditions at room temperature using an inert organic solvent such as dimethyl formamide (DMF). The esters are insoluble in water but soluble in methanol, acetone, ethanol, chloroform, pentane, benzene, ether and the like.

Furthermore, it has been found that when a composition containing a compound represented by formulas I and II, is applied to fruit-bearing trees the force required to remove the fruit from the stem is thereby significantly reduced in comparison to that required to remove the fruit from untreated trees (abscission). Further, fruit removed from trees with the aid of the compositions of the present invention has been found to be relatively free from pitting and rotting.

The compositions of the present invention can be applied to the fruit-bearing trees in liquid or solid formulations. Application may be made to the roots, trunks, limbs, leaves or fruit. For example, the normal abscission composition according to the present invention can be sprayed or dusted on the trees from airplanes or applied to the base of the trees in order to be absorbed by the roots. The preferred method of application and the most efficient is to apply the compositions in the form of an aqueous spray. If desired, a formulation based on suitable organic solvents may be used e.g. an oily spray.

In order to achieve the most efficient use of the normal abscission compositions of the present invention, it is preferred to apply them from about 1 to 2 weeks prior to harvesting of the fruit depending on the temperature. In areas where a rainfall is expected subsequent to application but prior to harvesting, a conventional sticking agent may be incorporated into the compositions. Typical examples of such sticking agents include glue, casein, salts of alginic acids, cellulose gums and their derivatives, polyvinyl pyrrolidone, vegetable gums, invert syrup, corn syrup and the like.

Compositions of this invention contain as an essential active ingredient a compound represented by formulas I and II. If desired, inert materials conventionally used in agriculture for application to trees may be utilized in conjunction with the active ingredients of the normal abscission compositions of the present invention. Such adjuvants include, for example, surface active agents, carriers, sticking agents, stabilizers and the like.

The concentration of the compounds represented by formulas I and II suitable for use in the novel abscission compositions of the present invention vary, but, in order to be most effective, it is necessary that a sufficient amount be present to provide from about 0.05% to about 1.5% by weight of the active compound in an aqueous spray solution. This amount will naturally vary according to the fruit to be sprayed and the size of the tree or bush. The application rate is that which is effective in facilitating harvesting. For spray applications, the aqueous solution containing the abscission composition is applied to the tree until run-off. In commercial operations this involves the application of from 300 l to 9000 l of a dilute spray solution (~0.1–1% by wt. of active ingredient) per hectare, depending upon the number and size of the trees sprayed.

In order to form the preferred liquid spray formulations embodying the abscission compositions of the present invention, the active ingredients or a salt thereof are dispersed or dissolved in a carrier such as, for example, water. From about 0.1% to about 0.5% by weight, based on the weight of the carrier, of a surface active agent may be included in the liquid spray compositions. Typical surface active agents are Triton -B- 1956, a water-dispersible, resin-based surfactant manufactured by Rohm and Haas and X-77 (Chevron-Ortho) a non-ionic type composition containing as the principal functioning agent alkylaryl-polyoxyethylene glycols, free fatty acids and isopropanol.

The abscission compositions of this invention effectively abscind a variety of fruits from trees. Typical fruits with which these compositions are efficacious include oranges, grapefruits, olives, apples, cherries, tomatoes and the like. They are also efficacious in use with other crops such as cotton (to drop the leaves) and soybeans.

As has been stated, it is preferred to apply the novel abscission compositions of the present invention to fruit trees in the form of an aqueous spay. In this respect, it is within the purview of the present invention to utilize equivalent amounts of the water soluble salts of the compounds represented by Formulas I and II. Such salts include for example the sodium salt, the potassium salt, the ammonium salt and the like.

The novel abscission compounds of this invention are buffered to a pH range of 6–10 by the addition of potassium hydrogen phosphate to the aqueous solution.

In those cases where the compounds to be used are not soluble in water, emulsifiable concentrates or wettable powder formulations of the active ingredients are prepared which can be dispersed in water to form the spray solutions.

Wettable powders are prepared using an inert diluent, e.g., kaolin. A typical spray solution formulated with a wettable powder would contain the active ingredient, from about 1% to about 5% of an inert diluent, minor amounts of dispersing, wetting and anti-foaming agents and, the balance, water.

The efficacy of the novel abscission compositions of the present invention may be illustrated in the following greenhouse screening tests on *Phaseolus vulgaris* (red kidney bean).

The compounds to be evaluated on *Phaseolus vulgaris* are formulated as wettable powders and mixed with lanolin to form lanolin pastes containing 5000 and 1000 ppm of active ingredients.

In the method used, a seed in sown 1.5 cm deep in a small-plastic pot containing a mixture of 50% sterilized loam soil and 50% Optimasoil (containing 80% peat and 20% clay and fertilizer) of known physical and chemical characteristics. 14 days later when the primary leaves are fully developed the seedings are cut just above the surface of the soil. The stem is cut to a length of 2 cm. measured from the cotyledone. The petioles of the primary leaf are cut to a length of 0.5 cm and treated with the lanolin paste. The stems of the explants are kept in a small vessel in tap water for 5 days in the growth room. For each dosage 8 replications are used. The growth regulatory activity is assessed 4 and 6 days after treatment.

Petiole abscission is determined by counting the retained petioles. The extent of abscission is expressed as a percentage of the corresponding value obtained with untreated plants.

Test results are provided in the following table IV.

Table IV

Determination of abscission activity on Phaseolus vulgaris (red kidney bean)

| Compound | % Petiole abscission Concentration (ppm) | |
|---|---|---|
| | 5000 | 1000 |
| Cyanomethyl 2,3:4,5-di-O-isopropylidene-2-keto-D-gluconate | 100 | 50 |
| Sodium 2,3:4,5-di-O-isopropylidene-2-keto-D-gluconate | 55 | 40 |
| 2-Propynyl 2,3:4,5-di-O-isopropylidene-2-keto-D-gluconate | 70 | 15 |
| Ammonium 2,3:4,5-di-O-isopropylidene-2-keto-D-gluconate | 50 | 50 |
| Allyl 2,3:4,5-di-O-isopropylidene-2-keto-D-gluconate | 45 | 40 |
| n-Pentyl 2,3:4,5-di-O-isopropylidene-2-keto-D-gluconate | 45 | 45 |
| n-Propyl 2,3:4,5-di-O-isopropylidene-2-keto-D-gluconate | 20 | 15 |
| n-Hexyl-2,3:4,5-di-O-isopropylidene-2-keto-D-gluconate | 20 | 15 |
| n-Dodecyl 2,3:4,5-di-O-isopropylidene-2-keto-D-gluconate | 25 | 20 |
| n-Butyl 2,3:4,5-di-O-isopropylidene-2-keto-D-gluconate | 20 | 15 |
| n-Octyl 2,3:4,5-di-O-isopropylidene-2-keto-D-gluconate | 15 | 20 |
| 3-Chloropropyl 2,3:4,5-di-O-isopropylidene-2-keto-D-gluconate | 15 | 15 |
| 4-Chloroethyl 2,3:4,5-di-O-isopropylidene-2-keto-D-gluconate | 5 | 5 |
| 2-Chloroethyl 2,3:4,5-di-O-isopropylidene-2-keto-D-gluconate | 0 | 5 |

The following Examples illustrate the invention.

EXAMPLE 1

2,3:4,5-di-O-isopropylidene-$\beta$-D-fructopyranose

A mixture of 200 grams of D-fructose, 2 liters of acetone, 2 liters of pentane and 8 grams of ferric chloride is stirred and heated to reflux temperature. The reaction water is condensed and removed using a Dean-Stark type water separator. After the theoretical amount of water is removed, the mixture is cooled to 0°C., neutralized with 7 grams of sodium hydroxide in 10 milliliters of water and filtered. The filtrate is treated with 10 grams Norite SG, refiltered, and then concentrated to a syrup which is crystallized from ether-pentane to give 164.4 grams of product, m.p. 94°–95°C.

EXAMPLE 2

Ammonium salt of 2,3:4,5-di-O-isopropylidene-2-keto-D-gluconic acid

To a solution of 23.8 grams of potassium hydroxide and 15.8 grams of potassium permanganate in 250 ml. of water is added, with stirring, 26 grams of 2,3:4,5-di-O-isopropylidene-$\beta$-D-fructopyranose, prepared as described in Example 1 above. The solution is heated to 50°–60°C. with stirring and maintained thereat for 2 hours. An additional 15.8 grams of potassium permanganate is then added and stirring is continued overnight at 50°–60°C. The solution is filtered and the filtrate, after concentrating to about 125 grams, is cooled to 0°C., acidified to pH 2.0 and extracted 3 times with methylene chloride. Methylene chloride is removed from the combined extracts and concentrated ammonium hydroxide is added. Evaporation of the excess ammonia under vacuum yields the ammonium salt which is recrystallized from chloroform to give 13.5 grams, m.p. 190°–200°C. (dec.). Both TLC and GLPC analyses show the product to be pure.

Analysis: Calc'd. for $C_{12}H_{21}NO_7$(%): C, 49.48; H, 7.27; N, 4.81. Found (%): C, 49.30; H, 7.39; N, 4.42.

EXAMPLE 3

By procedures analogous to those of Examples 1 and 2, various disubstituted gluconic acids and their salts can be prepared. For example, using diethyl ketone in place of acetone in Example 1, the 2,3:4,5-di-O-(3-pentylidene)-2-keto-D-gluconic acid is prepared. Using methyl ethyl ketone in place of acetone, the 2,3:4,5-di-O-(2-butylidene)-2-keto-D-gluconic acid is prepared. Using cyclohexanone, the 2,3:4,5-di-O-cyclohexylidene-2-keto-D-gluconic acid is prepared. With chloral as the reactant, 2,3:4,5-di-O-(2,2,2-trichloro ethylidene)-2-keto-D-gluconic acid is prepared. In like manner other gluconic acid derivatives are prepared wherein $R_1$, $R_2$, $R_3$ and $R_4$ are hydrogen, straight or branched chain aliphatic lower hydrocarbyl, halo-lower alkyl or aryl or where $R_1$ and $R_2$ together and $R_3$ and $R_4$ together are saturated rings of from 3 to 8 carbon atoms.

EXAMPLE 4

Methyl-2,3:4,5-di-O-isopropylidene-2-keto-D-gluconate

To a stirred suspension of 10 g. of anhydrous potassium carbonate in 75 ml. of dimethylformamide was added 33.7 g. of 2,3:4,5-di-O-isopropylidene-2-keto-D-gluconic acid and then 25 g. of methyl iodide. The mixture was stirred over a 3 day period at room temperature and then filtered to remove any inorganic salts. Dimethylformamide was then removed by vacuum distillation.

20 Ml. of acetone were added to dissolve the ester residue. Undissolved inorganic salts were removed by filtration. The resulting filter cake was washed with 10 ml. of acetone. This filtrate was combined with the ester solution and concentrated under vacuum to a syrup. Vacuum distillation at 92°C. at ~ 0.1 mm yielded 19.4 grams of liquid methyl 2,3:4,5-di-O-isopropylidene-2-keto-D-gluconate.

Analysis Calc'd. for $C_{13}H_{20}O_7$ (%): C, 54.16; H, 6.99. Found (%): C, 54.47; H, 7.13.

$[\alpha]_D^{25°} = 52.9°$ ($c = 1$).

EXAMPLE 5

Ethyl ester of 2,3:4,5-di-O-isopropylidene-2-keto-D-gluconic acid

To a stirred suspension at room temperature of 10 g. of anhydrous potassium carbonate in 75 ml. of dimethylformamide were added 33.7 g. of 2,3:4,5-di-O-isopropylidene-2-keto-D-gluconic acid followed by 25 g. of ethyl bromide. Stirring was continued over a 3 day period at room temperature. The mixture was then filtered to remove any inorganic salts, dimethylformamide was removed by vacuum distillation (ca. 60° and ca. 10 mmHg) and 20 ml. of acetone were added to dissolve the ester residue. Any undissolved inorganic salts were removed by filtration. The resulting filter cake was washed with 10 ml. of acetone. This filtrate was combined with the ester solution and the crude product was isolated therefrom by vacuum reduction of the solvent. Vacuum distillation at 94°C. and ~ 0.1 mm yielded 16.4 g. of ethyl 2,3:4,5-di-O-isopropylidene-2-keto-D-gluconate.

Analysis Calc'd. for $C_{14}H_{22}O_7$ (%): C, 55.62; H, 7.34. Found (%): C, 55.80; H, 7.41.

$[\alpha]_D^{25°} = -46.59°$ (C = 1.7405).

Following this general procedure using 2,3:4,5-di-O-isopropylidene-2-keto-D-gluconic acid and 1,2-dibromoethane in a 2:1 mole ratio, the bis ester: Bis-2,3:4,5-di-O-isopropylidene-2-keto-D-gluconate, ethylene glycol ester, is prepared. Using a 1:1 mole ratio, 2-bromoethyl 2,3:4,5-di-O-isopropylidene-2-keto-D-gluconate is prepared.

EXAMPLE 6 n-Butyl-2,3:4,5-di-O-isopropylidene-2-keto-D-gluconate

To a stirred suspension of 10 g. of anhydrous potassium carbonate in 75 ml. of dimethylformamide was added 33.7 g. of 2,3:4,5-di-O-isopropylidene-2-keto-D-gluconic acid and then 25 g. of n-butyl bromide. THe mixture was stirred over a 3 day period at room temperature and then filtered to remove any inorganic salts. Dimethylformamide was removed by vacuum distillation. 20 Ml. of acetone were added to dissolve the ester residue. Any remaining inorganic salts were removed by filtration. The resulting filter cake was washed with 10 ml. of acetone. This filtrate was combined with the ester solution and concentrated under vacuum to the crude product which was purified by vacuum distillation at 96°C. and ~0.1 mm. to yield 19.7 g of n-butyl 2,3:4,5-di-O-isopropylidene-2-keto-D-gluconate.

Analysis Calc'd. for $C_{16}H_{26}O_7$(%): C, 58.17; H, 7.93. Found (%): C, 58.33; H, 8.13.

In a similar manner other straight and branched chain aliphatic hydrocarbyl and halo-lower alkyl esters can be prepared.

EXAMPLE 7

2,3-O-isopropylidene-4,5-O-ethylidene-2-keto-D-gluconic acid, sodium salt.

48 grams of 2,3:4,5-di-O-isopropylidene-2-keto-D-gluconic acid were dissolved in 250 grams of paraldehyde. Five drops of 70% perchloric acid were added and the reaction was continued for 12 days at room temperature under monitoring by Thin Layer (TLC) or Gas Liquid Chromatography (GLC). This solution was then added with vigorous stirring to 16.8 grams of a sodium bicarbonate slurry in 100 ml of water. Any excess paraldehyde and water were removed under vacuum. The residue was recrystallized from an alcohol/water mixture to yield the sodium salt of 2,3-O-isopropylidene-4,5-O-ethylidene-2-keto-L-gluconic acid. Physical chemical data (n.m.r., Mass spectra, infrared) show the structure to be:

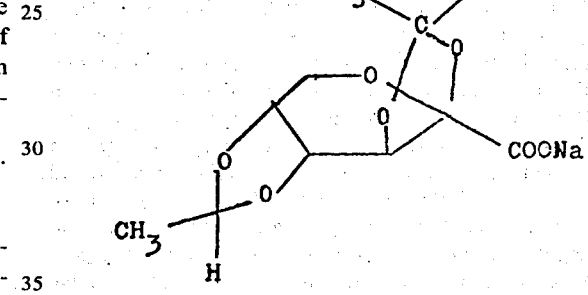

In like manner, other 2,3-O-isopropylidene-4,6-O-($R_1$-$R_2$)-2-keto-L-gluconic acids, (structure I) where the $R_1$ and $R_2$ substituents are straight and branched chain aliphatic lower hydrocarbyl, halo-lower alkyl, aryl or $R_1$ and $R_2$ together, a saturated ring of from 3 to 8 carbon atoms can be prepared.

EXAMPLE 8

2-Chloroethyl-2,3:4,5-di-O-isopropylidene-2-keto-D-gluconate.

6 g of 2,3:4,5-di-O-isopropylidene-2-keto-D-gluconic acid (water free) are dissolved in 14 ml of pyridine and 3.2 ml methylene chloride. With stirring and ice cooling dropwise 3.2 ml thionyl chloride are added to the mixture which was then kept for 3 hours at room temperature. Thereafter 5.9 ml of 2-chloroethanol are added and stirring is continued for additional 3 hours. Then the reaction mixture is extracted with methylene chloride and the methylene chloride phase is washed with 2N-hydrochloric acid, 2N-sodium hydroxide solution and water. The organic phase is dried over sodium sulfate and evaporated. The residue is purified on a silica gel column and thereafter distilled. Boiling point: 129°C/0.02 Torr.

I claim:

1. A compound represented by the formula

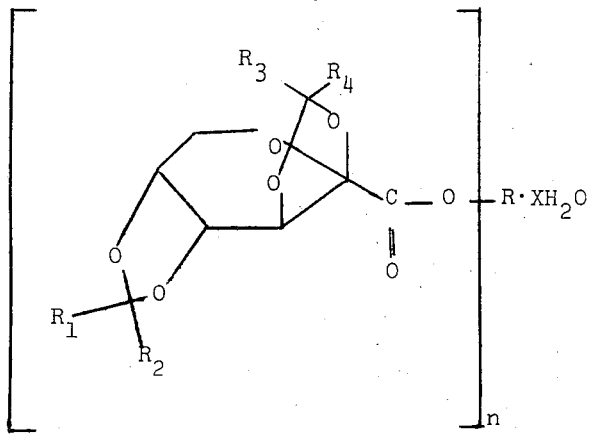

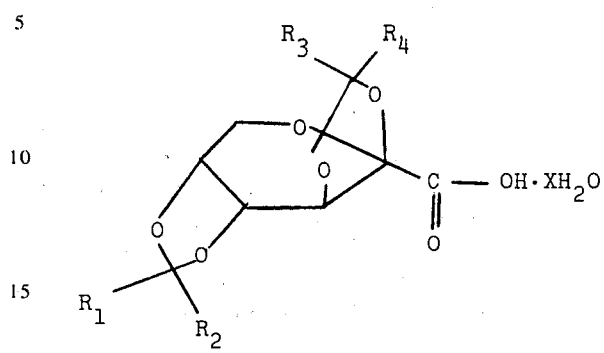

wherein, when n is 1, R is straight or branched chain alkyl of from 1 to 12 carbon atoms, straight or branched chain lower alkenyl, straight or branched chain lower alkynyl, or halo-lower alkyl and, when n is 2, R is lower alkylene; $R_1$, $R_2$, $R_3$ and $R_4$ are hydrogen, straight or branched chain lower alkyl, straight or branched chain lower alkenyl, straight or branched chain lower alkynyl, halo-lower alkyl, phenyl, mono-(lower alkoxy) phenyl or $R_1$ and $R_2$ together and $R_3$ and $R_4$ together are each a saturated ring containing from 3 to 8 carbon atoms and wherein the combination of the substituents of $R_1$ and $R_2$ is the same as the combination of the substituents of $R_3$ and $R_4$; n is an integer from 1 to 2 and X is a number from 0 to 1.

2. A compound in accordance with claim 1, wherein $R_1$, $R_2$, $R_3$ and $R_4$ are methyl.

3. A compound in accordance with claim 2, methyl 2,3:4,5-di-O-isopropylidene-2-keto-D-gluconate.

4. A compound in accordance with claim 2, ethyl 2,3:4,5-di-O-isopropylidene-2-keto-D-gluconate.

5. A compound in accordance with claim 2, n-butyl 2,3:4,5-di-O-isopropylidene-2-keto-D-gluconate.

6. A compound in accordance with claim 2, n-dodecyl 2,3:4,5-di-O-isopropylidene-2-keto-D-gluconate.

7. A compound in accordance with claim 2, n-propyl 2,3:4,5-di-O-isopropylidene-2-keto-D-gluconate.

8. A compound in accordance with claim 2, n-pentyl 2,3: 4,5-di-O-isopropylidene-2-keto-D-gluconate.

9. A compound in accordance with claim 2, benzyl 2,3:4,5-di-O-isopropylidene-2-keto-D-gluconate.

10. A compound in accordance with claim 2, n-decyl 2,3:4,5-di-O-isopropylidene-2-keto-D-gluconate.

11. A compound in accordance with claim 2, isoamyl 2,3:4,5-di-O-isopropylidene-2-keto-D-gluconate.

12. A compound in accordance with claim 2, 2-butyl 2,3:4,5-di-O-isopropylidene-2-keto-D-gluconate.

13. A compound in accordance with claim 2, 2-bromoethyl-2,3:4,5-di-O-isopropylidene-2-keto-D-gluconate.

14. A compound in accordance with claim 2, bis-2,3:4,5-di-O-isopropylidene-2-keto-D-gluconate, ethylene glycol ester.

15. A compound represented by the formula wherein $R_1$, $R_2$, $R_3$ and $R_4$ are hydrogen, straight or branched chain lower alkyl, straight or branched chain lower alkenyl, straight or branched chain lower alkynyl, halo-lower alkyl, phenyl, mono-(lower alkoxy) phenyl or $R_1$ and $R_2$ together and $R_3$ and $R_4$ together are each a saturated ring containing from 3 to 8 carbon atoms and X is a number from 0 to 1 and wherein the combination of the substituents of $R_1$ and $R_2$ is the same as the combination of the substituents of $R_3$ and $R_4$ and at least one of $R_1$, $R_2$, $R_3$ and $R_4$ is a substituent other than methyl.

16. A compound in accordance with claim 15, 2,3:4,5-di-O-methylene-2-keto-D-gluconic acid.

17. A compound in accordance with claim 15, 2,3:4,5-di-O-ethylidene-2-keto-D-gluconic acid.

18. A compound in accordance with claim 15, 2,3:4,5-di-O-(3-pentylidene)-2-keto-D-gluconic acid.

19. A compound in accordance with claim 15, 2,3:4,5-di-O-(2-butylidene)-2-keto-D-gluconic acid.

20. A compound in accordance with claim 15, 2,3,4,5-di-O-cyclohexylidene-2-keto-D-gluconic acid.

21. A compound in accordance with claim 15, 2,3:4,5-di-O-benzylidene-2-keto-D-gluconic acid.

22. A compound in accordance with claim 15, 2,3:4,5-di-O-(p-methoxybenzylidene)-2-keto-D-gluconic acid.

23. A compound in accordance with claim 15, 2,3:4,5-di-O-(2-chloroethylidene)-2-keto-D-gluconic acid.

24. A compound in accordance with claim 15, 2,3:4,5-di-O-(1,3-dichloroisopropylidene)-2-keto-D-gluconic acid.

25. A compound in accordance with claim 15, 2,3:4,5-di-O-(1,1,3-trichloroisopropylidene)-2-keto-D-gluconic acid.

26. A compound in accordance with claim 15, 2,3:4,5-di-O-(1,1,1,3-tetrachloroisopropylidene)-2-keto-D-gluconic acid.

27. A compound in accordance with claim 15, 2,3:4,5-di-O-(2,2-dichloroethylidene)-2-keto-D-gluconic acid.

28. A compound in accordance with claim 15, 2,3:4,5-di-O-(1,1,3,3-tetrachloroisopropylidene)-2-keto-D-gluconic acid.

29. A compound in accordance with claim 15, 2,3:4,5-di-O-(2,2,2-trichloroethylidene)-2-keto-D-gluconic acid.

30. A compound in accordance with claim 15, 2,3:4,5-di-O-(2-fluoroethylidene)-2-keto-D-gluconic acid.

31. A compound in accordance with claim 15, 2,3:4,5-di-O-(1,3-difluoroisopropylidene)-2-keto-D-gluconic acid.

32. A compound in accordance with claim 15, 2,3:4,5-di-O-(1,1,3-trifluoroisopropylidene)-2-keto-D-gluconic acid.

33. A compound in accordance with claim 15, 2,3:4,5-di-O-(1,1,1,3-tetrafluoroisopropylidene)-2-keto-D-gluconic acid.

34. A compound in accordance with claim 15, 2,3:4,5-di-O-(2,2-difluoroethylidene)-2-keto-D-gluconic acid.

35. A compound in accordance with claim 15, 2,3:4,5-di-O-(1,1,3,3-tetrafluoroisopropylidene)-2-keto-D-gluconic acid.

36. A compound in accordance with claim 15, 2,3:4,5-di-O-(1,1,1,3,3-pentafluoroisopropylidene)-2-keto-D-gluconic acid.

37. A compound in accordance with claim 15, 2,3:4,5-di-O-(2,2,2-trifluoroethylidene)-2-keto-D-gluconic acid.

38. A compound in accordance with claim 15, 2,3:4,5-di-O-(1,1,1,3,3,3-hexafluoroisopropylidene)-2-keto-D-gluconic acid.

39. A compound in accordance with claim 15, 2,3:4,5-di-O-(2-bromoethylidene)-2-keto-D-gluconic acid.

40. A compound in accordance with claim 15, 2,3:4,5-di-O-(1,3-dibromoisopropylidene)-2-keto-D-gluconic acid.

41. A compound in accordance with claim 15, 2,3:4,5-di-O-(1,1,3-tribromoisopropylidene)-2-keto-D-gluconic acid.

42. A compound in accordance with claim 15, 2,3:4,5-di-O-(2,2-dibromoethylidene)-2-keto-D-gluconic acid.

43. A compound in accordance with claim 15, 2,3:4,5-di-O-(1,1,3,3-tetrabromoisopropylidene)-2-keto-D-gluconic acid.

44. A compound in accordance with claim 15, 2,3:4,5-di-O-(2,2,2-tribromoethylidene)-2-keto-D-gluconic acid.

45. A compound in accordance with claim 15, 2,3:4,5-di-O-(1,1,1-tribromoisopropylidene)-2-keto-D-gluconic acid.

* * * * *